United States Patent [19]
Bare et al.

[11] 4,126,126
[45] Nov. 21, 1978

[54] NON-METALLIC PREGELLED ELECTRODE

[75] Inventors: Rex O. Bare; Earl F. Robinson, both of Lawrence; Kevin R. Smith, Leawood, all of Kans.

[73] Assignee: C. R. Bard, Inc., Murray Hill, N.J.

[21] Appl. No.: 709,140

[22] Filed: Jul. 27, 1976

[51] Int. Cl.² .............................................. A61B 5/04
[52] U.S. Cl. ............................ 128/2.06 E; 128/2.1 E; 128/417; 128/DIG. 4; 339/176 P; 339/195 R
[58] Field of Search .............. 128/2.06 E, 2.1 E, 404, 128/410, 411, 416, 417, 418, DIG. 4; 339/176 P, 195 R, DIG. 3

[56] References Cited

U.S. PATENT DOCUMENTS

| | | | |
|---|---|---|---|
| 2,755,452 | 7/1956 | Rogie | 339/176 P X |
| 2,943,628 | 7/1960 | Howell | 128/418 |
| 3,170,459 | 2/1965 | Phipps | 128/2.06 E |
| 3,187,745 | 6/1965 | Baum et al. | 128/2.06 E |
| 3,229,241 | 1/1966 | Kao | 339/DIG. 3 X |
| 3,340,868 | 9/1967 | Darling | 128/2.06 E |
| 3,580,240 | 5/1971 | Cosentino | 128/2.06 E |
| 3,599,629 | 8/1971 | Gordy | 128/2.06 E |
| 3,848,600 | 11/1974 | Patrick, Jr. et al. | 128/417 X |
| 3,973,557 | 8/1976 | Allison | 128/2.06 E |
| 3,976,055 | 8/1976 | Monter et al. | 128/2.06 E |
| 4,051,842 | 10/1977 | Hazel et al. | 128/2.06 E |

FOREIGN PATENT DOCUMENTS 2,147,413  3/1973  Fed. Rep. of Germany ....... 339/176 P

OTHER PUBLICATIONS

Agard et al., "Coaxial Cable . . . Connector", IBM Technical Disclosure, vol. 13, No. 6, Nov. 1970, p. 59.

Primary Examiner—Lee S. Cohen
Attorney, Agent, or Firm—Dennison, Dennison, Meserole & Pollack

[57] ABSTRACT

An electrode pad, an electrical lead wire connector, and an electrode system composed of the pad and connector which exhibits a DC offset of about 1mV, an AC impedance of less than 100Ω, and a stable rectification of less than 0.2mV.

The electrode pad of the system, for attachment to the skin for detecting biological or physiological electrical potentials, includes an electrically non-conductive disc, an electrolyte saturated porous matrix in the disc and integral provision for attaching an electrical connector, the pad having no metal components.

The electrical connector has an electrically conductive probe at one end composed of a non-conductive plastic with a conductive silver and silver chloride coating thereover.

14 Claims, 10 Drawing Figures

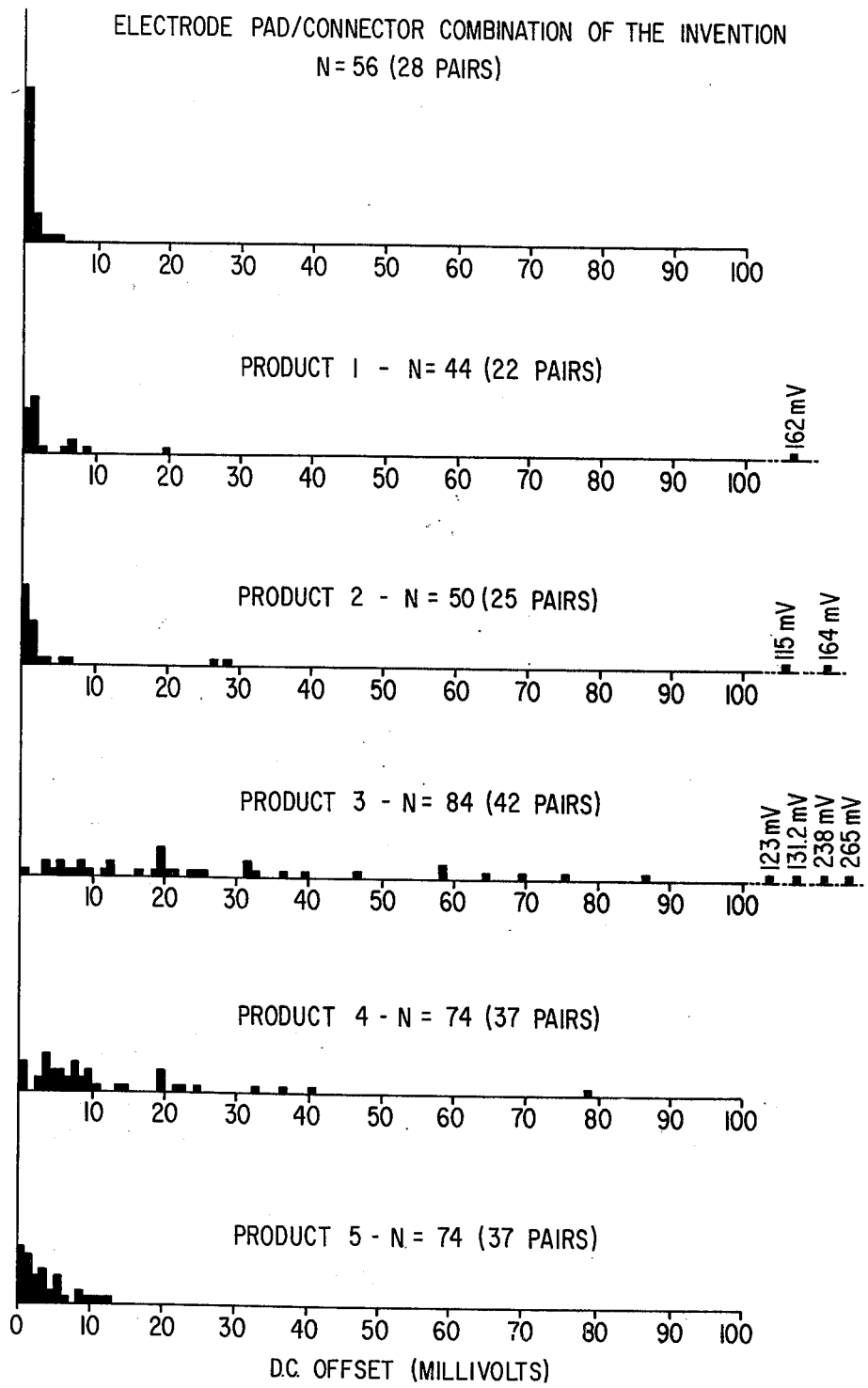

NON-METALLIC PREGELLED ELECTRODE

BACKGROUND OF THE INVENTION

This invention relates to skin electrodes, and more particularly to pregelled disposable medical electrodes used to detect biological or physiological electrical potentials such as those associated with muscular activity. In more detail, this invention relates to low cost, high quality pregelled electrocardiogram (ECG) electrodes for detecting the muscular activity of the human heart.

Most ECG electrodes in routine use today depend on a metal-electrolyte interface with the body surface. Many electrodes use extremely pure silver as the metallic component. Those in which a moist, ready-to-use electrolytic paste is packaged as part of the electrode are termed pre-gelled. Electrodes intended for single patient use only are considered disposable. Those that can be reused many times are termed permanent.

In the past, the only high quality electrodes available contained pure silver as the metallic component of the electrode, with the surface often chlorided to achieve optimum performance. The process of chloriding involves coating, either by electrodeposition or reaction with chlorine gas, of the active surface of the silver with a thin layer of silver chloride.

Conventional permanent ECG electrodes are available in many styles and configurations, but all share several negative characteristics, these characteristics not being evident in the present invention:

(a) They are often relatively expensive, since most employ high cost construction materials and methods.

(b) They must be reprocessed (cleaned carefully) between uses.

(c) They must be attached to the skin with separate straps, suction cups, glue, tape, adhesive pads, or similar means.

(d) Most require that electrolytic gel or fluid be applied to the skin (or electrode) at time of use.

(e) Most are "short term" electrodes (in the sense that they cannot be left on a patient for more than a few hours before the gel desiccates and loses its electrical contact with the skin).

On the positive side, the best properly-prepared permanent ECG electrodes are capable of delivering extremely high resolution, nearly artifact-free signals. Hence, they are used whenever very high quality "Type I" ECG recordings are necessary. Further, if preparation and reprocessing costs are ignored. the cost/use is low, compared to pregelled, single-use electrodes. Suction or strap-attached permanent electrodes are often used when short-term ECG's are needed, since the electrodes can be repositioned or moved as often as necessary without resorting to the use of tape or glue.

Conventional disposable ECG electrodes offer increased convenience over permanent electrodes. Disposable ECG electrodes are usually pregelled, self-adhesive, and clean. Since they cannot be reused, cross-contamination is minimized and postuse cleanup is minimal. Most electrodes of this type provide reasonably accurate transduction of ECG data and are a fairly cost-effective approach to routine diagnostic ECG's and heart rate monitoring. Most will function adequately for one to several days, depending on the patient.

Pregelled electrodes typically consist of a thin, adhesive coated disc of open or closed cell foam or microporous tape. A centrally located gel reservoir consisting of a molded cup, such as shown in U.S. Pat. Nos. 3,696,807, 3,701,346, 3,713,435, 3,820,531 or 3,830,229, or a die cut hole in the foam, such as shown in U.S. Pat. No. 3,868,946, encapsulates a gel-saturated open cell compressible foam column. In the alternative, the gel-saturated, open cell foam column may be adhered directly to the face of the disc of foam, such as in U.S. Pat. No. 3,828,766, or to an impermeable backing material as in U.S. Pat. No. 3,805,769. The consistency of the gel is maintained by sealing the opening of the gel reservoir in one of several ways, which include: an injection molded or thermo-formed cap removably attached to the gel cup or an adhesive coated film on the disc in conjunction with a moisture-proof backing paper attached to the film and covering the gel saturated foam column or a combination of these. In spite of the use in these electrodes of such means for sealing the gel reservoir, most also require a secondary air-tight foil pouch or plastic bag to contain the electrode in an air-tight way and preserve the gel in a usable condition.

All pregelled electrodes known to be presently available, incorporate a metallic component in contact with the gel. This component can be silver coated plastic, silver, nickel, or stainless steel. In some types of electrodes, lead wires are permanently attached to the electrode. In the majority, however, a male snap fastener of silver, stainless steel, nickel, etc., is incorporated as a part of the electrode. A lead wire having a mating metallic female snap fastener on one end is connected to the male snap fastener of the electrode. The opposite end of such lead wire is then secured to a diagnostic instrument, such as a cardiograph. As an alternative, a silver-coated plastic snap fastener, such as shown in U.S. Pat. No. 3,841,312 may be used. Use of mating snap fasteners have the disadvantage that relative movement between the electrode and the lead may cause motion artifacts. Further, use of a coated plastic male snap in conjunction with a metallic female snap may result in the silver coating on the male snap being scratched off during application or usage, causing faulty readings.

U.S. Pat. No. 3,599,629 shows an electrode which does not employ a snap fastener. Instead, this device has a flat, wafer-like top composed of an electrically insulating material coated with a thin film of metallic silver having a surface layer that has been converted to silver chloride. Rather than using a wire lead having a mating snap fastener, this electrode employs a tubular plug dimensioned to snugly fit into a corresponding silver chloride coated socket in the wafer-like top, electrical continuity resulting from intimate contact between the socket and the plug.

In all of the above instances, the pregelled electrodes are sold ready for use having an electrically conductive material, such as metal or a metal chloride, in contact with the electrolyte gel. Such contact presents the possibility of chemical reaction between the two during storage of the electrode prior to usage. In addition, in all known conventional pregelled electrodes, especially those containing silver or silver chloride, the metal component represents a considerable portion of the cost of the electrode. As the electrodes are disposed of after only one use, the cost of the metal adds considerably to the cost of usage of same.

SUMMARY OF THE INVENTION

The electrode system of the present invention includes an electrolyte-containing pad and a lead wire connector specifically designed to mate with the pad. Specifically, the present electrode pad is a low cost, disposable, pregelled type which does not have any metallic parts. This pad includes a flexible electrically non-conductive or insulative thermoplastic disc having a cavity in the center thereof and an electrolytesaturated gel matrix disposed and secured in said cavity. The matrix is composed of a porous flexible plastic material. An adhesive coating is provided on the lower surface of the disc and a release backing is adhered to the adhesive coating covering and hermetically sealing the electrolyte saturated gel matrix in the cavity. The electrode disc has lead wire mounting means molded into the upper portion thereof for receiving a special lead wire connector and holding it in contact with the gel saturated matrix.

The lead wire connector, hereafter termed a "connector" of the invention consists of an electrically conductive probe sized for secure mating with the mounting means in the electrode pad and a wire connected to the probe, the point of connection between the probe and the wire being hermetically sealed in a thermoplastic insulator. More specifically the probe is a unitary piece having two blades on the electrode mating end, said blades being connected by a central portion. Preferably the probe consists of an electrically non-conductive plastic having a coating of silver thereover and a film of silverchloride covering that portion of the silver coating extending beyond the thermoplastic insulator.

The pregelled electrode pad and connector combination of the invention forms a low cost disposable electrode system which has high fidelity signal transduction, negligible baseline drift, offset, and polarization and minimal distortion, artifacts or noise in the ECG output recording made during use of the electrode system, even after several continuous days of usage. This is accomplished by the use of a metal free electrode pad, a unique design connector and the construction of both which acts in conjunction to maintain an electrical circuit between the probe and an electrolyte gel in contact with the patient's skin. In addition, the electrode is easily applied and removed, is comfortable to wear over prolonged periods of time and is non-irritating to normal skin. If the electrode is constructed of a transparent material the user has the capability of observing the internal portions of the electrode prior to application of the pad and the patient's skin and electrical conduction path during usage to assure that sufficient electrolyte is present and that contact between the components is adequate. A prime advantage of the invention is the low cost per use which is a result of constructing an electrode pad which does not contain expensive metallic components or coatings which must be thrown away after each use.

BRIEF DESCRIPTION OF THE DRAWING

FIG. 10 is a bar chart comparing D.C. offset for the electrode of the invention with five different commercially available disposable pregelled electrodes.

DESCRIPTION OF THE PREFERRED EMBODIMENTS

Figure 1:
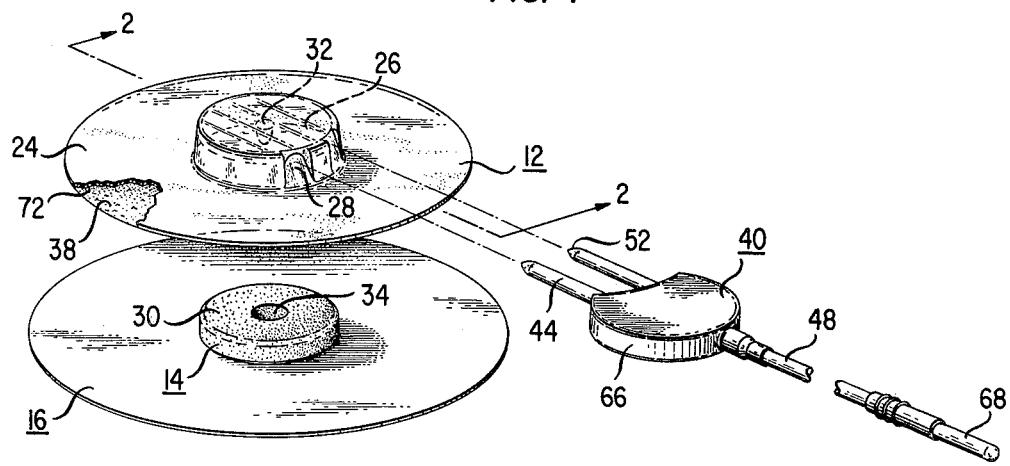
FIG. 1 is a perspective exploded view of an electrode pad and connector in accordance with the invention.
Figure 2:
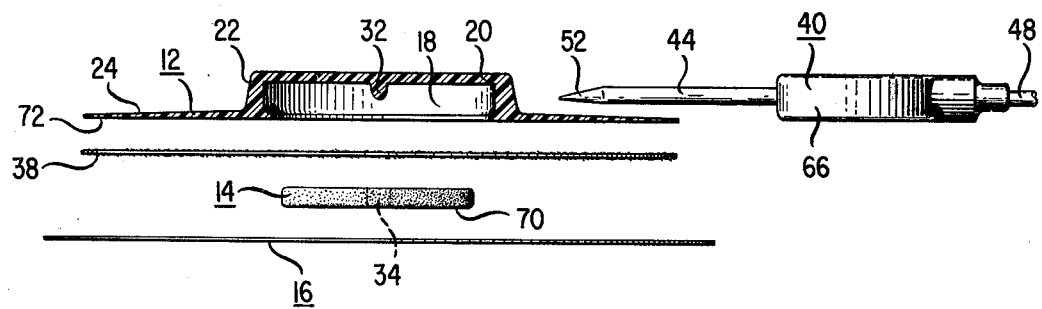
FIG. 2 is a cross sectional view of the electrode pad, taken along line 2—2 of FIG. 1 prior to insertion of the connector.

Referring now to the drawings, an electrode pad 10 constructed according to the principles of the present invention, is shown in FIGS. 1 and 2 in conjunction with a connector generally designated as 40. The electrode pad 10 consists of a disc 12, a gel matrix 14 located in a cavity 18 positioned in the center of said disc 12 and a release backing 16 covering the adhesive 38 coated lower face 72 of the disc 12 and the uncoated gel matrix 14. After removal of the release backing 16 the adhesive coated lower face 72 of the electrode is placed on a patient's skin, thus interfacing the gel matrix to the skin for ECG readings.

The disc 12 is formed of a thermoplastic material which preferably is flexible, can be readily molded to fit the contour of the patient's skin, and has low moisture absorption and high electrical resistance. Suitable materials include silicone rubber, natural rubber, thermoplastic rubber, polyvinyl chloride, polyurethane, or other flexible polymers. As an added feature, this material can be transparent so that the patient's skin can be continuously observed through the electrode pad 10 to detect possible skin changes and to permit easy inspection during usage of the adhesive/skin interface. The gel matrix 14 and a gel-connector-interface caused by mating of the electrode pad 10 and electrolead 40 is also readily observable.

The disc 12 is provided with a central cavity 18 defined by a cap 20, a vertically depending wall 22 and an annular ring 24 extending outward from the wall 22. The annular ring 24 may correspond in thickness to the height of wall 22 or preferably may be a tapered flange 24 extending from the lower edge of the wall 22 as shown in FIG. 2. The cavity in combination with the release backing 16 provides a moistureproof space capable of protecting electrolyte gel enclosed therein for extended periods of time. Elongated semi-circular slot 26 extends through the vertical wall 22 and into the inner surface of the cap 20. In the preferred embodiment two parallel slots 26 are used. However, one slot or more than two slots can be used. Until the electrode pad is put into service the slot or slots 26 extending through the wall 22 are maintained closed and impervious to moisture by membranes 28 or portions of the wall 22 having reduced thickness.

The gel matrix 14 consists of a non-conductive porous material of limited compressibility, such as compacted felt, non-woven fabric, a molded or extruded honeycomb of plastic, or other similar material. In the preferred embodiment, the gel matrix is formed of sintered thermoplastic, such as polyethylene, having a void volume of 20 to 60% of the total matrix volume. The gel matrix 14 is saturated with a suitable conductive electrolyte gel 30 conventionally used with electrocardiograph instruments, for example a gel of sodium chloride in agar. The gel matrix 14 is positioned in the cavity 18 by an indexing pin 32 which extends from the inner surface of the cap 20 into a central hole 34 in the matrix 14. The matrix 14 is retained in the cavity 18 by an annular lip 36 molded into wall 22, near the lower surface 72. To further retain the matrix 14 in the cavity 18 a small amount of adhesive material may be applied to the interface between the indexing pin 32 and the central hole 34 in the matrix 14.

Medical grade pressure sensitive adhesive 38, preferably transparent and moistureproof, is applied to the lower face 72 of the disc 12. A protective cover or backing 16 of an impervious release material, such as a polymer coated paper, completely covers the adhesive 38 and encloses the gel saturated matrix 14 in the cavity.

Figure 3:
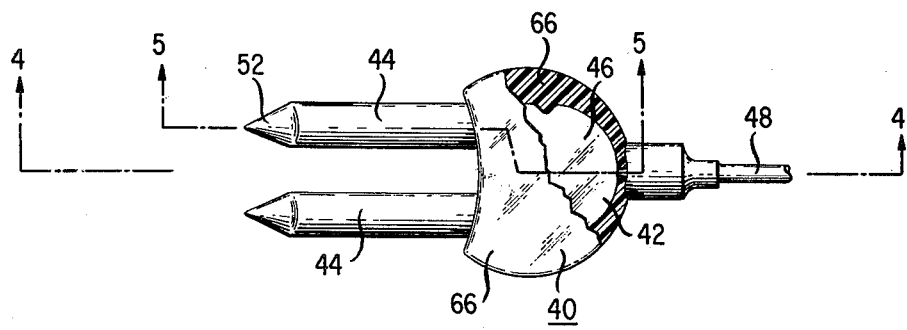
FIG. 3 is a top view of the connector to be used with the electrode pad of the invention.
Figure 4:
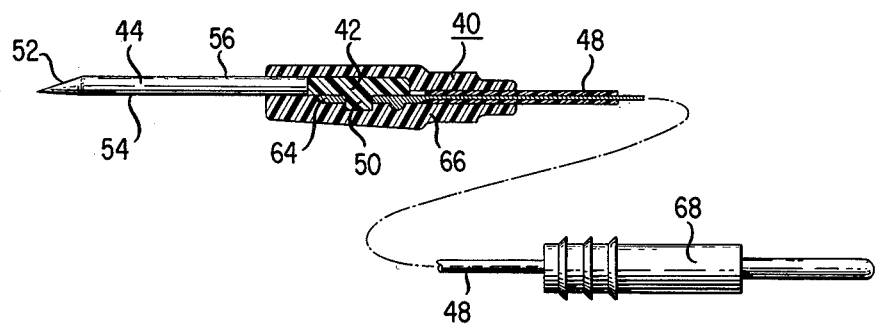
FIG. 4 is a partly cutaway cross sectional view of the connector taken along line 4—4 of FIG. 3 and further showing a plug at the free end of the wire.
Figure 5:
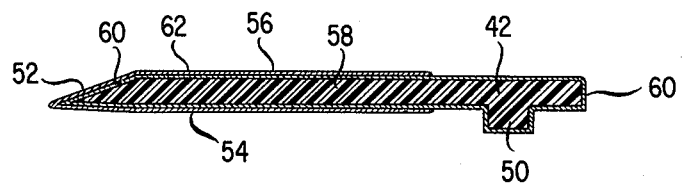
FIG. 5 is a cross sectional view of the probe taken along line 5—5 of FIG. 3. The dimensions of the coatings shown therein are not to scale but are exaggerated for clarity.

Referring to FIGS. 3, 4 and 5, the connector 40 consisting of an insulation boot 66, probe 42 mounted in the insulation boot 66, the probe 42 having blades 44 extending from one end of the insulation boot 66 and an electrical wire 48 extending from the other end of insulation boot 66, the electrical wire 48 and the probe 42 being secured to each other within insulation boot 66.

Figure 9:
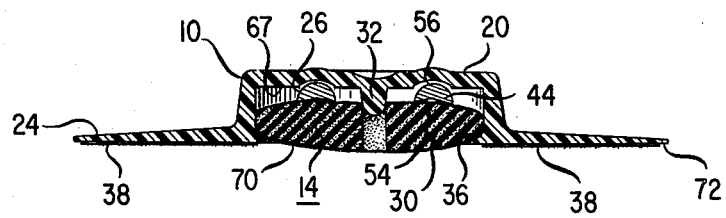
FIG. 9 is a cross sectional view of the electrode pad taken along line 9—9 of FIG. 7 after insertion of the connector.

The electrically conductive probe 42 is designed to pierce thin sections of the wall 22, such as membrane 28, so that it fits snugly into the blade slot 26. In the preferred embodiment, the electrically conductive probe is a unit having two parallel blades 44 and a central portion 46 connected to an insulated wire 48. Connection of the wire 48 to the probe 42 is made by stud 50 attached to or molded into the lower surface of central portion 46 of the probe 42. As shown in FIGS. 3, 5 and 9, the blades 44 have sharp tips 52, a broad or flattened bottom surface 54 and a rounded upper surface 56. The sharp tips 52 are designed to readily puncture the membrane 28 when the connector 40 is connected to the electrode 10. The broad bottom surface 54 of the blade 44 provides maximum contact with the gel matrix 14 while the rounded upper surface 56 and the resultant semi-circular cross-section of each blade functions to give the blades strength and stiffness and to hold the blades 44 in the slots 26 to prevent movement artifacts. The electrically conductive probe 42 may be made of a suitable conductive metal or a plastic having a conductive metal coating. In the preferred embodiment shown in FIG. 5 the probe is made of a non-conductive thermoplastic material 50, for example ABS (acrylonitrile butadine styrene polymer) having a silver coating 60 applied thereto, preferably electrodeposited thereon after the surface of the thermoplastic material is made conductive by known coating techniques. This electroplated silver forms a tough, crack-resistant conductive surface on the plastic. Using conventional methods a silver chloride layer 62 is then formed on the silver coating 60. The silver chloride layer 62 may be formed by chemically converting the outer portion of the silver coating 60 to silver chloride, such as by treatment with hydrochloric acid, or may be electrodeposited on top of the silver coating 60. In the preferred embodiment, the electrodeposited silver-chloride layer 62 has a uniform thickness of 20–5000 mA sec/cm$^2$, preferably 100–1000 mA sec/cm$^2$. The silver-chloride layer 62 has a dark color while the underlying silver coating 60 has a shiny appearance. Because of the hardness of the silver chloride layer 62 the connector 40 can be reused through several ECG procedures. However, extensive use or repeated cleaning may damage the silver chloride layer. Damage is readily apparent by the shiny silver showing through the dark colored silver chloride layer.

The design of the electrode pad 10 and connector 40 in combination makes possible high quality recording of ECG data. The first use of each connector provides a Type I recording with diagnostic accuracy similar to that previously obtained only with the highest quality hand made research electrodes. Depending on care taken in cleaning the connector, this Type I performance can be repeated through several subsequent uses of the same connector. Connector 40 used as many as 25 times still exhibit Type II recording performance, required for routine monitoring. Optimum performance continues through at least the first 10 usages. Eventually the silver chloride layer 62 will be worn away exposing the shiny underlying silver coating 60 thus signaling the operator to dispose of the connector.

Referring to FIGS. 3 and 4 the wire 48 is a standard multi-strand conductor commonly used for ECG leads. One end of the wire 48 terminates in a fitting 64 adapted to connect with probe 42. In the preferred embodiment, the wire 48 has a brass ring tongue fitting 64 which is sized to fit over the silver coated stud 50 in such a manner that when mated with stud 50 an electrical conductive path is formed between the probe 42 and the wire 48. The fitting 64 is securely attached to the stud 56 by staking or flattening of the stud and to the wire 48 by crimping or soldering.

The central portion 46 and the fitting 64 are encapsulated in a boot 66 composed of a thermoplastic electrically insulating material. This boot may be formed as two separate mating pieces designed to enclose the central portion 46 and the fitting 64 in which case central portion 46 and fitting 64 are assembled, the assembly is placed between the separate portions of boot 66 and the portions are securely attached together. Preferably, boot 66 is formed in one piece and is directly molded around the assembled central portion 46 and fitting 64. When the probe 42 is formed from ABS a suitable material for forming the boot is polyvinylchloride polymer (PVC). Molding the boot directly on to the central portion 46 and fitting 64 makes permanent the assembled unit and has the added advantage of hermetically sealing the junction between the connector 64 and central portion 46.

The other end of the wire 48 is secured to a plug 68 compatible with cardiograph equipment commonly used for ECG procedures.

Figure 6:
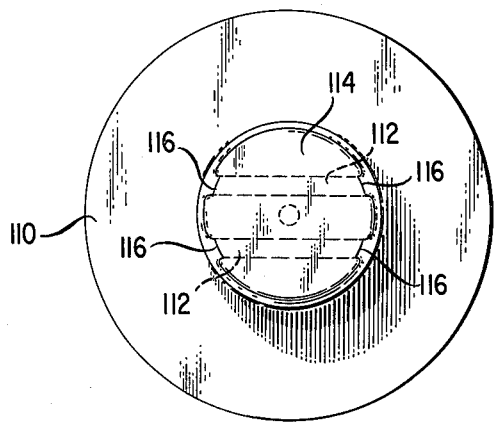
FIG. 6 is a top view of a second embodiment of the electrode pad in accordance with the invention.
Figure 7:
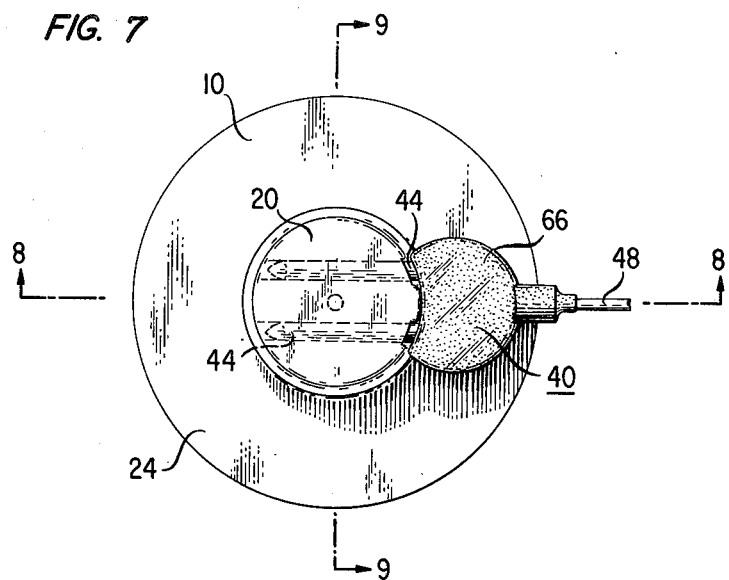
FIG. 7 is a top view of the electrode pad with the connector attached.

The embodiment of the invention shown in FIG. 6 consists of an electrode pad, generally designated as 110 having two blade slots 112 that extend completely across the cap 114 of the electrode. Membranes 116 correspond in function and design to the membranes 28, of the embodiment shown in FIGS. 1–2. Aside from the above all the other features of this embodiment correspond to the first embodiment described above. This embodiment has the additional advantage that blades 44 can be inserted from either side. It should be recognized that the invention described herein is not limited to the embodiments of the electrode specifically described but further encompasses electrodes constructed with one or more blade slots or pairs of blade slots, or a broad zone or band of puncturable membrane.

Figure 8:
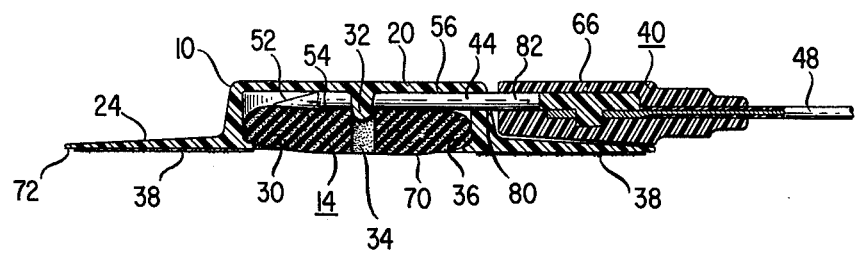
FIG. 8 is a cross sectional view of the electrode pad, taken along line 8—8 of FIG. 7 after insertion of the connector.

In use the electrode pad 10 and the connector 40 are connected by gripping the boot 66 of the connector in one hand and the electrode pad 10 in the other hand, aligning the sharp tips 52 of the blades 44 with the blade slots 26 and advancing the blades 44 forward into the slots 26 piercing the membranes 28 resulting in apertures 82, which are completely filled by blades 44 and which conform closely to the outer shape of the blades 44 so that electrode gel is prevented from exiting from cavity 18 through slots 26, and tight fitting flaps 80 that act to wipe the blade surfaces 54 and 56. Further advancement of the blade 44 forces portions of the gel matrix 14 down out of contact with the inner surface 67 of the cap 20. Because the gel matrix is not readily compressible, the insertion of the blades 44 pushes the lower portion or surface 70 of the gel matrix beyond the lower face 72 of the electrode pad 10 as shown in FIGS. 8 and 9. Also as shown in FIGS. 8 and 9, the insertion of blades 44 stretches that portion of the flexible cap 20 that is over the blades. The elastic, flexible nature of the cap 20 and the secure mounting of the gel matrix 14 cooperate to tightly hold the broad bottom surface 54 of blades 44 in intimate contact with the gel matrix 14 resulting in an electrically conductive path through the electrolyte gel 30 which fills the matrix 14, and the silverchloride layer 62 on the blade 44. In addition the tight mating of the blades 44 in the slots 26 serves to hold the connector 40 securely in the electrode pad 10. Use of indexing pin 32 further prevents relative movement between the electrode components and the connector 40, thus preventing disturbances of the ECG reading, known as motion artifact, which are common in electrodes which employ a snap type electrode connector.

The patient's skin is then prepared for attachment of the electrode pad 10 by standard cleaning procedures, possibly including shaving of the area. It is generally not necessary to abrade the skin surface to reduce skin impedance prior to application of the electrode pad, as is suggested procedure for use of many electrodes which employ compressible foam-like gel pads. The slightly abrasive lower surface 70 of the gel matrix 14 continuously performs the same function during usage of the electrode as is accomplished by abrasion of the skin prior to application of the electrode.

The release backing 16 is then removed from the lower face 72 of the electrode pad 10 and the electrode pad is applied to the patient's skin, the adhesive 38 firmly securing the electrode pad thereto and forcing the gel saturated matrix 14 into intimate contact with the skin. As indicated above, insertion of the blades 44 forces the gel matrix 14 to extend beyond the lower face 72 of the electrode pad 10 so that upon adhesive application of the electrode to the skin the gel matrix is forced into contact with the skin. The assembled combination of the electrode pad and connector forms a system uniquely designed to effect intimate and secure contact between the skin and all electrically conductive components so that artifact-free transmission of physiological potentials results.

Tests of electrode characteristics for quality control purposes were conducted on an electrode of the present invention and on various models of commercially available electrodes. These tests included AC impedance, DC offset and rectification. To perform the tests, the release backing 16 was removed from two like electrodes and these electrodes were placed face to face. The data obtained was for the pair; however, the resultant data is typical of normal usage, since the electrodes are normally applied in pairs.

AC impedance was determined by measuring the AC voltage drop across the electrode pair under test when a reference AC voltage is applied through the electrodes. DC offset was measured as the DC potential existing across the electrode pair when no AC or DC current is flowing. DC rectification was assessed by measuring the DC offset before and after application of a voltage, with rectification being defined as the difference between the two measurements.

No well established "ideal" values exist for any of these parameters. However, continuing tests show that "good" electrodes have AC impedance values of under 500Ω, depending on specific electrode configuration. DC offset values should be less than 10 mV, preferably less than 1 mV for Type I (diagnostic) monitoring. A number of commercial electrodes have DC offsets which are only a few mV and others are as high as 100 mV. DC rectification should be as small as possible, never exceeding 5 mV for Type I (diagnostic) monitoring electrodes.

The electrode system of the invention consistently demonstrates an AC impedance of less than 100Ω, as DC offset of about 1 mV and a rectification of less than 0.2 mV. Table 10 lists DC offset values for paired electrodes of the present invention compared with values obtained on several commercially obtained disposable pregelled electrodes measured using a Keithley Model 168 Digital Multimeter. The mean and median values obtained for the present invention are markedly superior to those obtained for the other samples tested. In addition, the commercially available samples, with the exception of Product 3, all showed a wide distribution of offset values. FIG. 10 is a bar chart showing the distribution of DC Offset Values obtained on all samples tested. From this Figure it is evident that the present invention would give more consistent and reliable readings. In addition, the electrode system of the invention shows a low frequency (0.5H$_z$) capacitive polarization significantly less than that exhibited by any other commercially available pregelled electrode, approximately the performance of a pure resistive element at 0.5H$_z$. This property permits more accurate transduction of low-frequency ECG wave components than any other commercially available disposable pregelled electrode.

TABLE 1

D. C. Offset (millivolts) of Electrode Pairs*

| Electrode | Sample Size (Pairs) | Mean | Median | Mode | Range |
|---|---|---|---|---|---|
| Invention | N = 28 | 1.03mV | 0.7mV | 1mV | 0–5mV |
| Product 2 | 25 | 15.02mV | 1.8mV | 1mV | 0–164mV |
| Product 1 | 22 | 12.48mV | 2.3mV | 2mV | 0–162mV |
| Product 5 | 37 | 4.21mV | 3.7mV | 1mV | 0–12mV |
| Product 4 | 40 | 12.43mV | 7.8mV | 4mV | 0–79mV |
| Product 3 | 42 | 45.24mV | 20.7mV | 20mV | 0–265mV |

*Measured using Keithley Model 168 Digital Multimeter

What is claimed is:

1. A medical electrode pad for attachment to the skin comprising a disk of electrically nonconductive material having a flat base and a centrally located cup shaped cavity therein, an electrolyte saturated porous plastic matrix received in said cavity, an adhesive on the surface of said flat base, and a release backing covering the adhesive surface and enclosing the matrix in the cavity; puncturable membrane means in said disc adapted to be punctured by a connector, and a removable electrically conductive connector inserted through and puncturing said membrane means and being in intimate contact with said electrolyte saturated porous plastic matrix.

2. An electrode pad as defined in claim 1 wherein said porous matrix is composed of a plastic material of limited compressibility.

3. An electrode pad as defined in claim 2, wherein said matrix is a porous polyethylene foam.

4. An electrode pad as defined in claim 1, and further including one or more connector guide slots formed in said disc adjacent to said membrane means for guiding said connector.

5. An electrode pad as defined in claim 1 wherein the disc is composed of a resilient, transparent plastic material.

6. A medical electrode pad having no metallic components for use on the skin for detecting biological electrical potentials comprising a one-piece disc of flexible electrically insulating thermoplastic material having a central cover element, a vertical periphery wall depending from said central cover element, said central element and vertical wall defining a central cavity, and a peripheral element having a lower surface extending out from said wall; a porous plastic matrix received in said central cavity; an electrolyte solution saturating said porous matrix and filling said central cavity; an adhesive covering said lower surface of said peripheral element; a release backing covering said adhesive and enclosing and hermetically sealing said plastic matrix and electrolyte solution in said cavity; and means in said cover element for receiving and guiding a removable electrically conductive probe into intimate contact with said matrix and electrolyte solution, said means for receiving and guiding the probe consisting of one or more slots in said cover element extending to said vertical wall, and a puncturable membrane sealing the slot or slots from the ambient.

7. The electrode of claim 6 wherein said porous plastic matrix has a limited compressibility.

8. A pad for detecting biological electrical potential comprising an electrically nonconductive one-piece disc formed with a central dome defining a recess in the pad, an electrically nonconductive porous matrix retained in and covered on its top and sides by said dome of the disc, an electrolyte solution contained in said matrix, said disc and matrix combination being disposable, and a reusable electrically conductive connector in contact with said matrix and the electrolyte solution and extending through the dome of said disc, said entire connector being removable from and separable from said dome and matrix through said dome.

9. The biological potential detecting device of claim 8 wherein the connector comprises a conductive probe mating with the disc and matrix combination, and a wire connected at one end to the probe and having at its other end a fitting for connection to biological potential recording means.

10. The biological potential detecting device of claim 9 wherein electrically insulating material seals the connection between the probe and the wire.

11. The biological potential detecting device of claim 9 wherein the probe comprises a non-conductive material having an electrically conductive coating on the surface thereof.

12. The biological potential detecting device of claim 9 wherein the probe comprises
   a non-conductive, thermoplastic material having an electrically conductive silver coating thereon, at least a portion of the probe being further coated with an electrically conductive silver chloride layer.

13. The biological potential detecting device of claim 9 wherein a boot of an electrically insulating material encloses the point of attachment of the wire to the probe, and said probe has a core of nonconductive material and a coating of an electrically conductive material.

14. The improved connector of claim 13 wherein the probe comprises an electrically non-conductive thermoplastic material having a silver coating thereover and a silver chloride coating covering at least part of said silver coating.

* * * * *